(12) United States Patent
Brighton (10) Patent No.: US 11,794,007 B1
(45) Date of Patent: Oct. 24, 2023

(54) METHOD AND DEVICE FOR STIMULATING BONE GROWTH

(71) Applicant: BonGenix, LLC, New York, NY (US)

(72) Inventor: Carl T. Brighton, Malvern, PA (US)

(73) Assignee: BonGenix, LLC, New York, NY (US)

( * ) Notice: Subject to any disclaimer, the term of this patent is extended or adjusted under 35 U.S.C. 154(b) by 0 days.

(21) Appl. No.: 17/966,209

(22) Filed: Oct. 14, 2022

Related U.S. Application Data (62) Division of application No. 17/878,756, filed on Aug. 1, 2022.

(51) Int. Cl.
| | |
|---|---|
| *A61N 1/32* | (2006.01) |
| *A61N 1/20* | (2006.01) |
| *A61N 1/36* | (2006.01) |
| *A61N 1/378* | (2006.01) |

(52) U.S. Cl.
CPC ............. *A61N 1/326* (2013.01); *A61N 1/205* (2013.01); *A61N 1/3603* (2017.08); *A61N 1/3787* (2013.01)

(58) Field of Classification Search
CPC ...... A61N 1/326; A61N 1/205; A61N 1/3603; A61N 1/3787
See application file for complete search history.

(56) References Cited

U.S. PATENT DOCUMENTS

| | | |
|---|---|---|
| 7,158,835 B2 | 1/2007 | Brighton et al. |
| 7,167,753 B2 | 1/2007 | Brighton et al. |
| 7,465,546 B2 | 12/2008 | Brighton |

(Continued)

FOREIGN PATENT DOCUMENTS

WO    WO-2007142901 A1 * 12/2007 ............. A61N 1/326

OTHER PUBLICATIONS

Inventor: Carl T. Brighton, Unpublished U.S. Appl. No. 17/878,756, filed Aug. 1, 2022, entitled Method and Device for Stimulating Bone Growth, 31 pp.

*Primary Examiner* — Catherine M Voorhees
(74) *Attorney, Agent, or Firm* — KAPLAN BREYER SCHWARZ, LLP (57) ABSTRACT

A bone stimulating method and device for treating injured or diseased bone tissue, includes exposing the injured or diseased bone tissue to a first electric field over a predetermined treatment period, the first electric field ranging from 10 mV/cm to 40 mV/cm and having a first predetermined time period within the predetermined treatment period and exposing the injured or diseased bone tissue to a second electric field over the predetermined treatment period, the second electric field ranging from 10 mV/cm to 60 mV/cm and having a second predetermined time period within the predetermined treatment period that is greater than the first predetermined time period. The first electric field is specific and selective for up-regulating expression of specific bone cell genes in the injured or diseased bone tissue when the injured or diseased bone tissue containing the specific bone cell genes is exposed to the first electric field and the second electric field is specific and selective for up-regulating expression of specific bone stem cell genes in the injured or diseased bone tissue when the injured or diseased bone tissue containing the specific bone stem cell genes is exposed to the second electric field.

15 Claims, 6 Drawing Sheets

(56) References Cited

U.S. PATENT DOCUMENTS

| | | | |
|---|---|---|---|
| 7,465,566 B2 * | 12/2008 | Brighton | A61N 1/40 607/50 |
| 7,981,611 B2 | 7/2011 | Brighton | |
| 8,016,369 B2 | 9/2011 | Breton et al. | |
| 8,065,015 B2 | 11/2011 | Brighton et al. | |
| 8,313,908 B2 | 11/2012 | Brighton | |
| 2011/0160811 A1 * | 6/2011 | Walker | A61N 1/0452 607/2 |
| 2012/0016442 A1 | 1/2012 | Brighton et al. | |
| 2012/0149968 A1 * | 6/2012 | Brighton | C12N 13/00 604/20 |

* cited by examiner

METHOD AND DEVICE FOR STIMULATING BONE GROWTH

RELATED APPLICATIONS

This application is a divisional of co-pending U.S. application Ser. No. 17/878,756, filed on Aug. 1, 2022, the entire disclosure of which is incorporated herein by reference.

FIELD

The present disclosure relates to up-regulating gene expression in target bone and stem cells and in particular, to a method and device for up-regulating the expression of those genes in bone and stem cells that can be induced to regulate bone growth and repair by application of specific and selective electric fields.

BACKGROUND

Bioelectrical interactions and activity are believed to be present in a variety of biological tissues, cells and stem cells. In particular, stimulation by electric and electromagnetic fields has been shown to stimulate growth and repair of bone and cartilage.

Methods currently exist where specific and selective electrical and electromagnetic signals are used to create electric and electromagnetic fields for up-regulating targeted genes in diseased or injured bone tissues. In addition, methods currently exist for up-regulating expression of the targeted genes in bone marrow stem cells. These genes belong to the BMP super family, and include BMP 2 and 4, FGF-2, and TGF-beta 1, 2, 3, alkaline phosphatase, and osteocalcin.

Therefore, non-invasive methods and devices are needed for treating osteoporosis, osteopenia, osteonecrosis, bone defects, fresh fractures, fractures at risk, delayed union, nonunion, and as an adjunct in spinal fusion.

SUMMARY

Disclosed herein is a non-invasive method for treating injured or diseased bone tissue. In various embodiments, the method comprises: exposing the injured or diseased bone tissue to a first electric field over a predetermined treatment period, the first electric field ranging from 10 mV/cm to 40 mV/cm and having a first predetermined time period within the predetermined treatment period; and exposing the injured or diseased bone tissue to a second electric field over the predetermined treatment period, the second electric field ranging from 10 mV/cm to 60 mV/cm and having a second predetermined time period within the predetermined treatment period that is greater than the first predetermined time period. The first electric field is specific and selective for up-regulating expression of specific bone cell genes in the injured or diseased bone tissue when the injured or diseased bone tissue containing the specific bone cell genes is exposed to the first electric field, and the second electric field is specific and selective for up-regulating expression of specific bone stem cell genes in the injured or diseased bone tissue when the injured or diseased bone tissue containing the specific bone stem cell genes is exposed to the second electric field.

Also disclosed herein is a non-invasive device for treating injured or diseased bone tissue. In various embodiments, the device comprises: an electrical signal generator; at least one memory storing instructions; a central processing unit for executing the instructions stored in the at least one memory, which causes the electrical signal generator to generate: a first electric field over a predetermined treatment period, the first electric field ranging from 10 mV/cm to 40 mV/cm and having a first predetermined time period within the predetermined treatment period; and a second electric field over the predetermined treatment period, the second electric field ranging from 10 mV/cm to 60 mV/cm and having a second predetermined time period within the predetermined treatment period that is greater than the first predetermined time period; and field generating devices electrically connected to the electrical signal generator, for exposing the injured or diseased bone tissue to the first and second electric fields. The first electric field is specific and selective for up-regulating expression of specific bone cell genes in the injured or diseased bone tissue when the injured or diseased bone tissue containing the specific bone cell genes is exposed to the first electric field and the second electric field is specific and selective for up-regulating expression of specific bone stem cell genes in the injured or diseased bone tissue when the injured or diseased bone tissue containing the specific bone stem cell genes is exposed to the second electric field.

In some embodiments, the first electric field is generated from a first capacitively coupled specific and selective signal having a frequency of 30 kHz to 80 kHz and a duty cycle ranging from 12.5% to 100%.

In some embodiments, the second electric field is generated from a second capacitively coupled specific and selective signal having a frequency of 30 kHz to 80 kHz and a duty cycle ranging from 50% to 100%.

In some embodiments, the specific bone cell genes and the specific bone stem cell genes whose expression is up-regulated by the first and second electric fields comprise BMP 2 and 4, TGF-beta 1, 2, and 3, FGF-2, BGP and ALP.

In some embodiments, the up-regulated expression of the specific bone cell and bone stem cell genes increases proteins levels of BMP 2 and 4, TGF-beta 1, 2, and 3, FGF-2, BGP and ALP in the injured or diseased bone tissue.

In some embodiments, the specific bone cell genes and the specific bone stem cell genes whose expression is up-regulated by the first and second electric fields increases protein levels of BMP 2 and 4, TGF-beta 1, 2, and 3, FGF-2, BGP and ALP in the injured or diseased bone tissue.

In some embodiments, the injured or diseased bone tissue is exposed to the first and second electric fields in a sequential manner.

In some embodiments, the first electric field is 20 mV/cm.

In some embodiments, the frequency of the first capacitively coupled specific and selective signal is 60 kHz.

In some embodiments, the duty cycle of the first capacitively coupled specific and selective signal is 50%.

In some embodiments, the first predetermined time period is 1 to 12 hours.

In some embodiments, the first predetermined time period is 2 hours.

In some embodiments, the second electric field is 20 mV/cm.

In some embodiments, the frequency of the second capacitively coupled specific and selective signal is 60 kHz.

In some embodiments, the duty cycle of the second capacitively coupled specific and selective signal is 50%.

In some embodiments, the second predetermined time period is 8 to 24 hours.

In some embodiments, the second predetermined time period is 12 hours.

In some embodiments, the predetermined treatment period is 12 to 48 hours.

In some embodiments, the predetermined treatment period is 48 hours.

In some embodiments, the injured or diseased bone tissue containing the specific bone stem cell genes is exposed to the second electric field 5 hours after the exposure of the injured or diseased bone tissue containing the specific bone cell genes to the first electric field has ended.

In some embodiments, the injured or diseased bone tissue containing the specific bone cell genes is exposed to the first electric field 5 hours after the exposure of the injured or diseased bone tissue containing the specific bone stem cell genes to the second electric field has ended.

In some embodiments, the field generating devices comprise a pair of conductive electrodes.

In some embodiments, the field generating devices comprise first and second pairs of conductive electrodes.

BRIEF DESCRIPTION OF THE DRAWING

The disclosure is best understood from the following detailed description when read in conjunction with the accompanying drawing. It is emphasized that, according to common practice, the various features of the drawing are not necessarily to scale. On the contrary, the dimensions of the various features may be arbitrarily expanded or reduced for clarity. Like numerals denote like features throughout the specification and the drawing.

DETAILED DESCRIPTION

It should be understood that the phraseology and terminology used below for the purpose of description and should not be regarded as limiting. The use herein of the terms "comprising," "including," "having," "containing," and variations thereof are meant to encompass the structures and features recited thereafter and equivalents thereof as well as additional structures and features. Unless specified or limited otherwise, the terms "attached," "mounted," "affixed," "connected," "supported," "coupled," and variations thereof are used broadly and encompass both direct and indirect forms of the same. Further, "connected" and "coupled" are not restricted to physical or mechanical connections or couplings.

The phrase "remote" is used to mean acting, acted on or controlled from a distance. "Remote" regulation refers to controlling the expression of a gene from a distance. To provide "remotely" refers to providing from a distance. For example, providing a specific and selective signal from a remote source can refer to providing the signal from a source at a distance from a tissue or a cell, or from a source outside of or external to the body.

The term "gene expression" means the up regulation of the process whereby specific portions (genes) of the human genome (DNA) are transcribed into mRNA and subsequently translated into protein.

The terms "up-regulate," up-regulates," "up-regulating," and "up-regulated" each means to increase expression of a gene.

A non-invasive bone growth stimulating method and corresponding bone growth stimulating device are disclosed herein, which use a Remote Gene Regulation (RGR) technique to non-invasively target and turn on specific genes in bone cells and stem cells in bone (bone stem cells) responsible for bone formation. The RGR techniques used in the bone stimulation method and device of the present disclosure comprises sequentially generating specific and selective first and second electric fields within diseased or injured target bone tissue of a patient. The first and second specific and selective electric fields can each be a pulsed electromagnetic field.

The first electric field is specific and selective for up-regulating the expression of certain genes in bone cells of the target bone tissue and the second electric field is specific and selective for up-regulating the expression of certain genes in bone stem cells of the target bone tissue. The genes in the bone cells and the bone stem cells, whose expressions are up-regulated by the sequentially applied first and second electric fields of the bone growth stimulation method and device of the present disclosure, are associated with governing the growth, maintenance, repair, and degeneration or deterioration of bone tissue. The expression of these genes can be up-regulated by the application of electric fields that are specific and selective for each gene or each set of complementary genes so as to produce a beneficial clinical effect. The bone growth stimulation method and device of the present disclosure provides targeted treatment of osteoporosis, osteopenia, osteonecrosis, fresh bone fractures, fractures at risk, nonunion, bone defects, spine fusion, and as an adjunct in the treatment of one or any of the above conditions. The bone stimulating method and device of the present disclosure up-regulates expression of certain the genes in bone cells and bone stem cells which include, without limitation, BMP 2 and 4; TGF-beta 1, 2, and 3; FGF-2; BGP (osteocalcin); and ALP (alkaline phosphatase), as measured by their corresponding mRNA and proteins found in the targeted bone tissue.

In one exemplary embodiment of the present disclosure, the bone growth stimulation method and device sequentially generate the specific and selective first and second electric fields within the targeted bone tissue using capacitive coupling methods techniques that use spaced apart field generating devices, such as self-adhering electrodes, which are applied to and touch the patient's skin in the vicinity of the targeted injured or diseased bone tissue and capacitively couple the first and second electric fields into the targeted bone tissue generated by the first and second specific and selective signals applied at the electrodes.

In one exemplary embodiment of the present disclosure, the bone growth stimulation method and device of the present disclosure specifically and selectively up-regulates gene expression in the targeted bone tissue in a patient's body by sequentially generating: 1) a first specific and selective signal that is applied for a first predetermined time period of 1 to 12 hours, to a first pair of field generating devices operatively disposed with respect to the targeted tissue, which causes the generation of a first specific and selective electric field of 10 mV/cm to 40 mV/cm in the targeted tissue; and 2) a second specific and selective signal that is applied for a second predetermined time period of 8 to 24 hours, to the first pair of field generating devices or to a second pair of field generating devices operatively disposed with respect to the targeted tissue, which causes the generation of a second specific and selective electric field of 10 mV/cm to 60 mV/cm in the targeted tissue. The targeted bone tissue is sequentially exposed to the first and second specific and selective electric fields (generated by the application of the first and second specific and selective signals to the field generating devices) for a treatment period of approximately 12 to 48 hours. The second specific and selective signal is applied to the field generating devices 5 hours after the application of the first specific and selective signal has ended and the first specific and selective signal is applied to the field generating device 5 hours after the application of the second specific and selective signal has ended. The first specific and selective signal generated by the bone growth stimulation method and device of the present disclosure typically has a sinewave waveform, a frequency of 30 kHz to 80 kHz, a peak-to-peak voltage of 1.0 to 12.0 volts depending upon the distance between the first pair of field generating devices and the nature of the targeted bone tissue, a peak-to-peak current of 5.0-30.0 milliamps depending upon the distance between the first pair of field generating devices and the nature of the targeted bone tissue, and a duty cycle ranging from 12.5% to 100%. The second specific and selective signal generated by the bone growth stimulation method and device of the present disclosure typically has a sinewave waveform, a frequency of 30 kHz to 80 kHz, a peak-to-peak voltage of 1.0 to 12.0 volts depending upon the distance between the first or second pair of field generating devices and the nature of the targeted bone tissue, a peak-to-peak current of 5.0-30.0 milliamps depending upon the distance between the first or second pair of field generating devices and the nature of the targeted bone tissue, and a duty cycle ranging from 50% to 100%.

Figure 1:
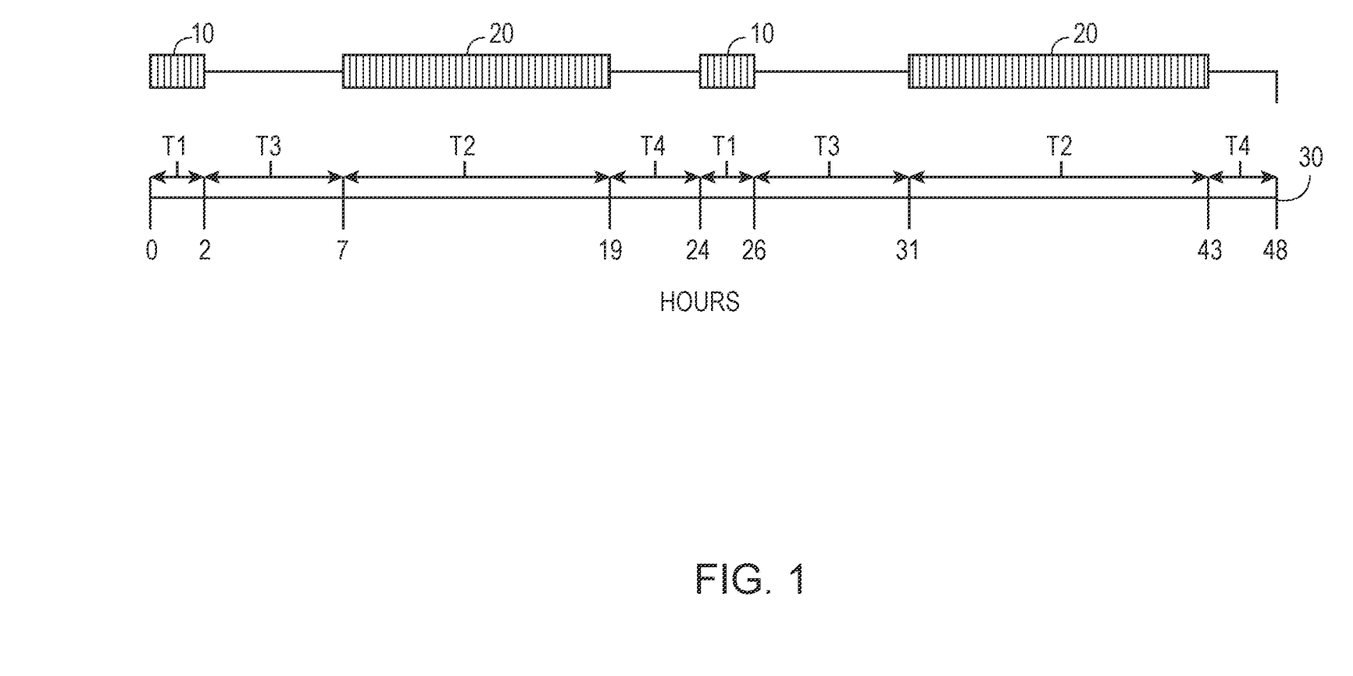
FIG. 1 graphically illustrates the sequentially generated first and second specific and selective signals that are applied to field generating devices and capacitively coupled into the targeted bone tissue according to a preferred embodiment of the bone growth stimulation method and device of the present disclosure.

FIG. 1 graphically illustrates the sequentially generated first and second specific and selective signals that are applied to field generating devices and capacitively coupled into the targeted bone tissue according to a preferred embodiment of the bone growth stimulation method and device of the present disclosure. As illustrated, the bone growth stimulation method and device of the present disclosure specifically and selectively up-regulates gene expression in the targeted bone tissue in a patient's body by sequentially generating: 1) a first specific and selective signal 10 that when applied for a first predetermined time period T1 of 2 hours to a first pair of field generating devices operatively disposed with respect to said targeted tissue causes the generation of a first specific and selective electric field of 20 mV/cm in the targeted tissue; and 2) a second specific and selective signal 20 that when applied for a second predetermined time period T2 of 12 hours to the first pair of field generating devices or to a second pair of field generating devices operatively disposed with respect to the targeted tissue causes the generation of a second specific and selective electric field of 20 mV/cm in the targeted tissue. The targeted bone tissue is sequentially exposed to first and second specific and selective electric fields (generated by the application of the first and second specific and selective signals 10 and 20 to the field generating devices) for a treatment period 30 of 48 hours. The second specific and selective signal 20 is applied to the field generating devices 5 hours (time period T3) after the application of the first specific and selective signal 10 has ended and the first specific and selective signal 10 is applied to the field generating devices 5 hours (time period T4) after the application of the first and specific and selective signal 10 has ended. The first specific and selective signal 10 generated by the bone growth stimulation method and device of the present disclosure preferably has a sinewave waveform, a frequency of 60 kHz, a peak-to-peak voltage of 1.0 to 12.0 volts depending upon the distance between the first pair of field generating devices and the nature of the targeted bone tissue, a peak-to-peak current of 5.0-30.0 milliamps depending upon the distance between the first or second pair of field generating devices and the nature of the targeted bone tissue, and a duty cycle of 50%. The second specific and selective signal generated by the bone growth stimulation method and device of the present disclosure preferably has a sinewave waveform, a frequency of 60 kHz, a peak-to-peak voltage of 1.0 to 12.0 volts depending upon the distance between the first or second pair of field generating devices and the nature of the targeted bone tissue, a peak-to-peak current of 5.0-30.0 milliamps depending upon the distance between the first or second pair of field generating devices and the nature of the targeted bone tissue, and a duty cycle of 50%.

The sequential application of the first and second specific and selective signals in the above-described manner, increases the overall levels of bone forming proteins by as much as an additional 40% over just using the first or the second specific and selective signals. This result allows the treatment duration to be further reduced, as compared to using just the first or the second specific and selective signals, while still increasing the rate of bone formation.

The bone growth stimulating devices of the present disclosure can be portable or can be temporarily or permanently attached to a patient's body. The bone growth stimulating devices of the present disclosure are preferably non-invasive in that the field generating devices can be applied to the skin of a patient in the form of conductive electrodes adapted for contact with the skin of a patient for capacitively coupling the sequentially applied first and second specific and selective signals that generate the specific and selective first and second electrical fields in the targeted bone tissue.

Figure 2:
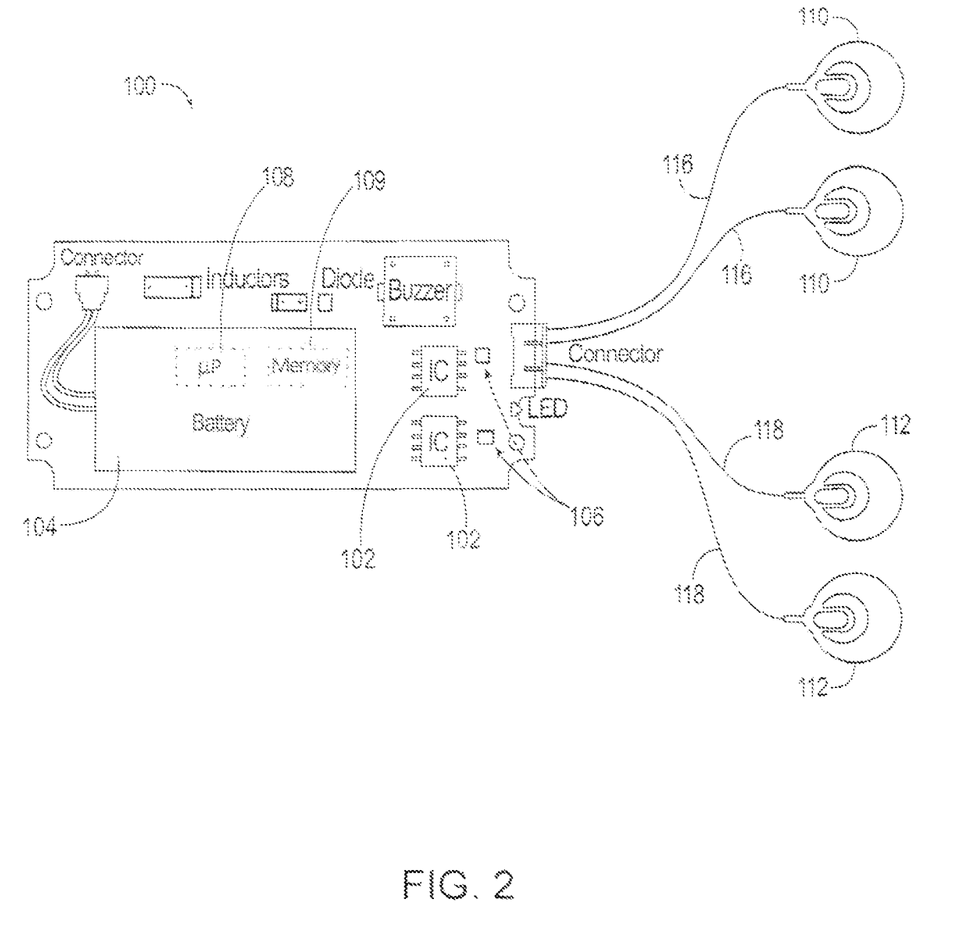
FIG. 2 schematically illustrates an exemplary embodiment of the bone growth stimulating device of the present disclosure.

FIG. 2 schematically illustrates an exemplary embodiment of the bone growth stimulating device of the present disclosure, denoted by reference character 100. The bone growth stimulating device 100 comprises an electrical signal generator comprising one or more integrated circuits 102 and transformers 106, powered by a battery 104 or other suitable power source. The one or more integrated circuits 102 take the current/voltage supplied by the battery 104 and create current/voltage signals, which are stepped up by the transformers 106. The electrical signal generator is monitored and controlled by a central processing unit (e.g., microprocessor 108). The microprocessor 108 is configured to retrieve and execute programming instructions stored in one or more memories 109, which can be a component of (e.g., a flash memory) and/or separate from (e.g., an EPPROM memory) the microprocessor 108. The one or more memories 109 include non-transitory, processor-readable mediums comprising the instructions, which programming instructions cause the microprocessor 108 to control the electrical signal generator so that it generates the first specific and selective signal according to the parameters (e.g., waveform, frequency, voltage, current, duration, and duty cycle) of the present disclosure delivered at a first pair of field generating devices 110 (e.g., self-adhesive conductive electrodes placed on the skin adjacent the diseased or injured bone tissue) and the second specific and selective signal according to the parameters (e.g., waveform, frequency, voltage, current, duration, and duty cycle) of the present disclosure delivered at a second pair of field generating devices 112 (e.g., self-adhesive conductive electrodes placed on the skin adjacent the diseased or injured bone tissue). The field generating devices 110 and 112 are electrically connected to the device 100 via electrical lead pairs 116 and 118, respectively.

Figure 3:
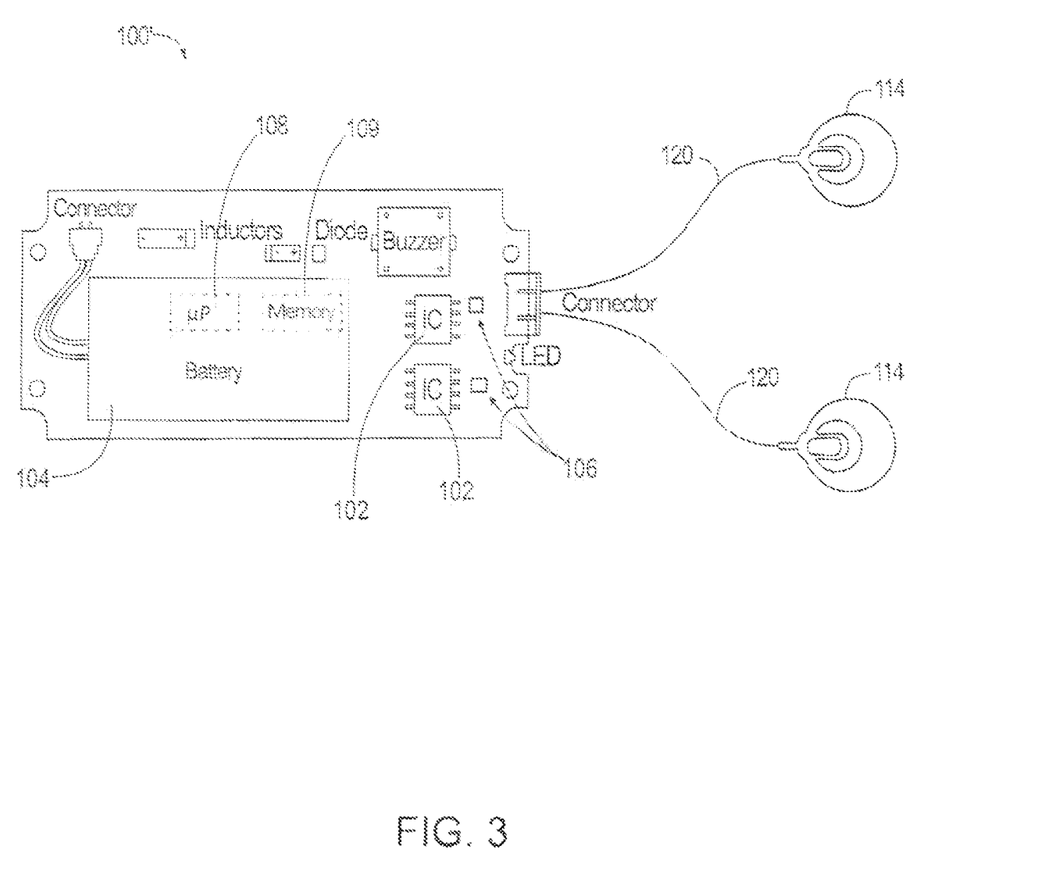
FIG. 3 schematically illustrates another exemplary embodiment of the bone growth stimulating device of the present disclosure.

FIG. 3 schematically illustrates another exemplary embodiment of the bone growth stimulating device of the present disclosure, denoted by reference character 100'. The bone growth stimulating device 100' is substantially identical to the bone growth stimulating device 100 of FIG. 2. However, in this embodiment, the first and second specific selective signals are each delivered at a single pair of field generating devices 114 (e.g., self-adhesive conductive electrodes placed on the skin adjacent the diseased or injured bone tissue). The field generating devices 114 are electrically connected to the device 100' via electrical lead pair 120.

Figure 4:
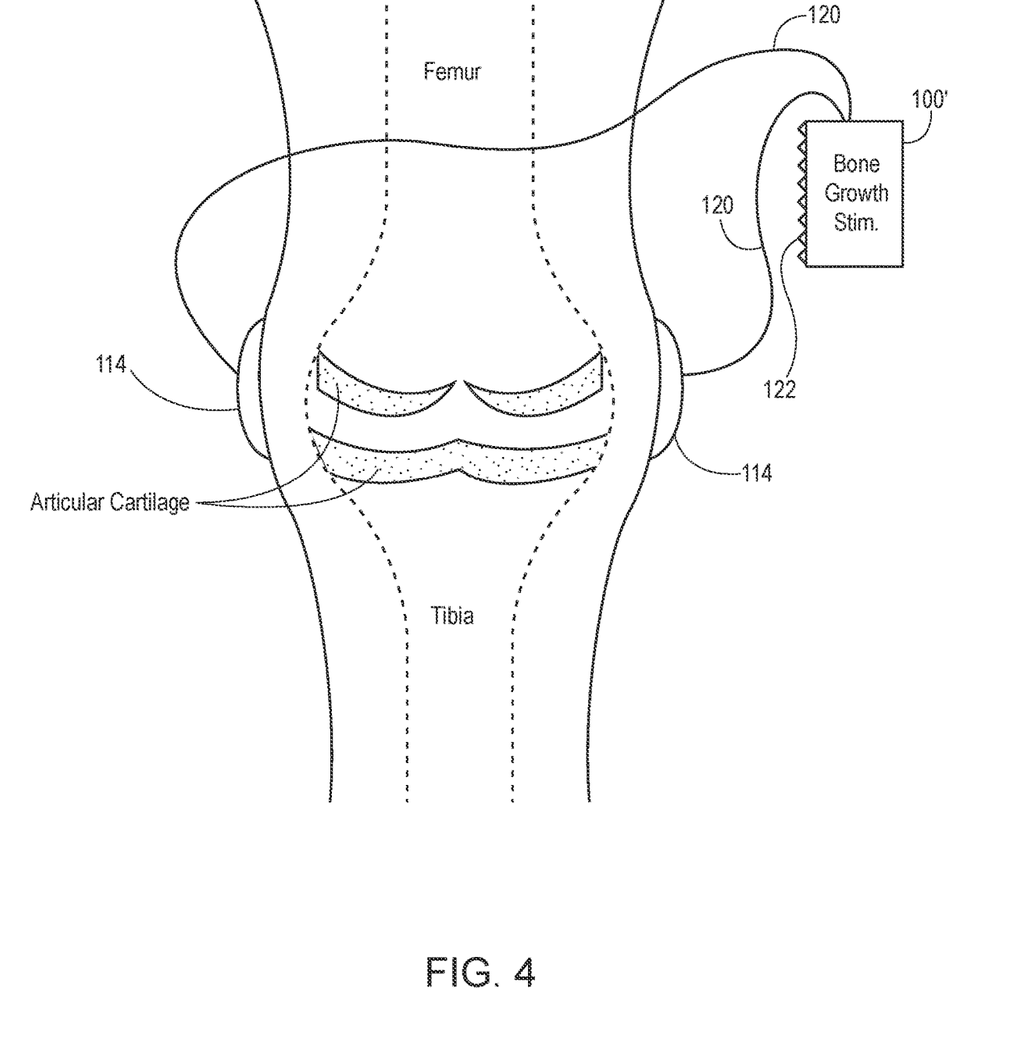
FIG. 4 schematically illustrates an exemplary use of the bone growth stimulating device of FIG. 3 for the treatment of osteoarthritis of the knee.

FIG. 4 illustrates an exemplary use of the bone growth stimulating device 100' of FIG. 3 to treat a patient having a knee joint afflicted with osteoporosis. As illustrated, the field generating devices in the form of self-adhesive conductive electrodes 114 are attached to the skin of the patient on both sides of that knee joint. The electrodes 114 are attached to the device 100' via electrical leads 120. The device 100' can be provided with a first member of a hook and loop fastener 122 such that the device 100' can be attached to a second member of a hook and loop fastener configured as a strap (not shown) fitted around the calf, thigh or waist. The electrodes 114 may be placed on the skin before the patient goes to bed each evening or any other convenient time. In some embodiments, the entire bone growth stimulating device 100, 100' of the present disclosure can be configured to attach the body of a patient and can include conductive electrodes integrated into a surface of the device (not shown), which can be attached to a strap fitted around the calf, thigh, or waist using a hook and loop fastener arrangement.

Figure 5:
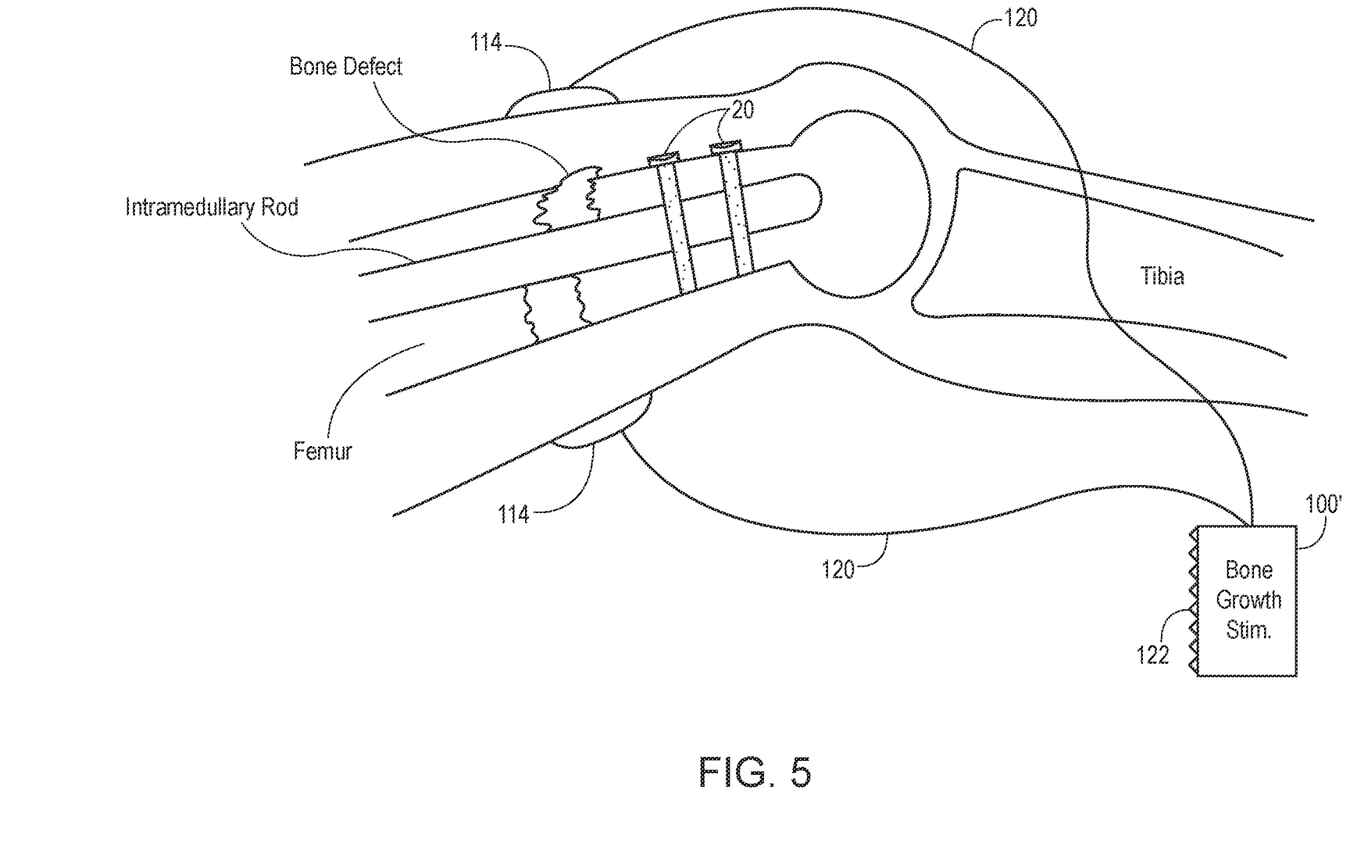
FIG. 5 schematically illustrates an exemplary use of the bone growth stimulating device of FIG. 3 for the treatment of a nonunion fracture of the femur stabilized by an intramedullary rod that is locked by two transcortical screws.

FIG. 5 illustrates an exemplary use of the bone growth stimulating device 100' of FIG. 3 to treat a patient with a fracture, delayed union, nonunion or other bone defect. In this application, the self-adhesive conductive electrodes 114 are placed on the skin on opposite sides of the extremity at the level of the defect so that the electrodes 114 so that they span the bone defect. As in the previously described, the device 100' can be provided with a first member of a hook and loop fastener 122 such that the device 100' can be attached to a second member of a hook and loop fastener configured as a strap (not shown) fitted around the calf, thigh or waist. As illustrated, the femur may be stabilized by an intramedullary rod 18 locked by two transcortical screws 20.

Figure 6:
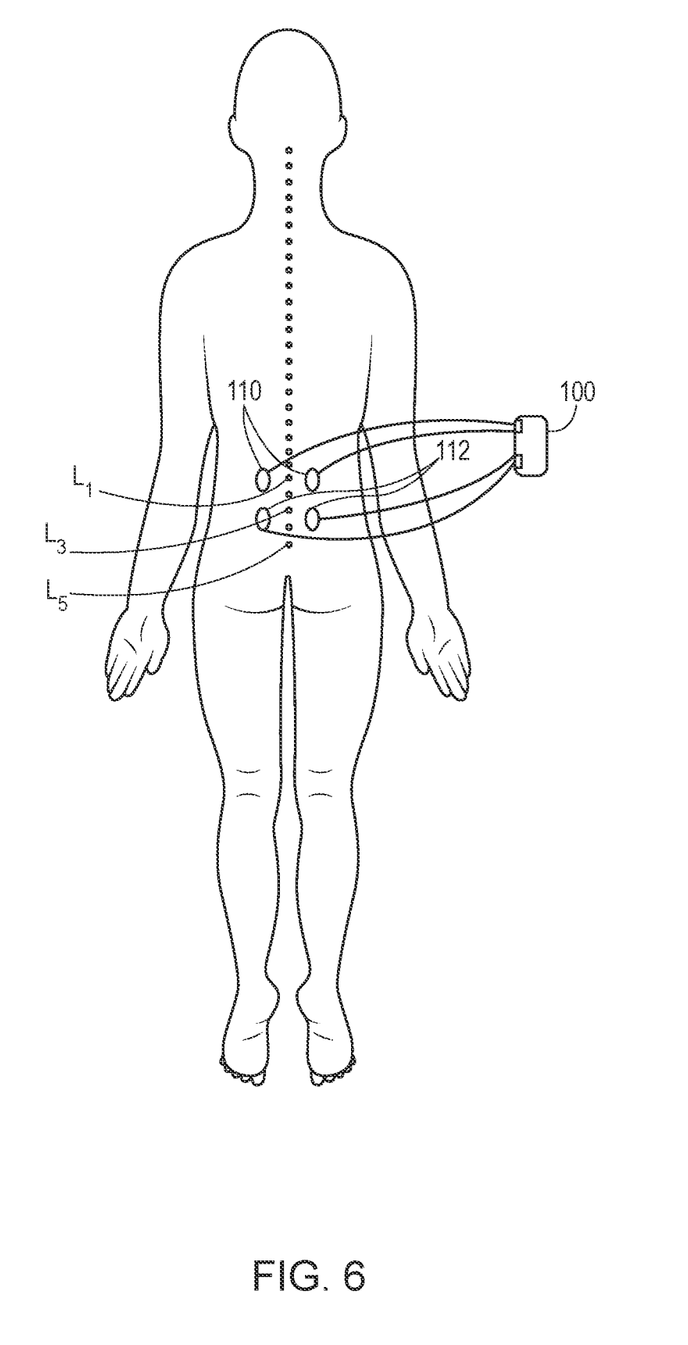
FIG. 6 schematically illustrates an exemplary use of the bone growth stimulating device of FIG. 4 for the treatment osteoporosis of the spine.

FIG. 6 illustrates an exemplary use of the bone growth stimulating device 100 of FIG. 2 to treat for osteoporosis. The device 100 can be worn in a cloth pocket bag that is held at the waist with a cloth belt or can be slipped into any pocket in the patient's clothing. The field generating devices 110 and 112 in the form of conductive electrodes can be adhesively attached to the patient's back with conductive gel on either side of the lumbar spine at the L1 to the L5 levels to capacitively couple the sequentially generated electrical fields into the lumbar spine.

It should be understood that the invention is not limited to the embodiments illustrated and described herein. Rather, the appended claims should be construed broadly to include other variants and embodiments of the invention, which may be made by those skilled in the art without departing from the scope and range of equivalents of the invention. It is indeed intended that the scope of the invention should be determined by proper interpretation and construction of the appended claims and their legal equivalents, as understood by those of skill in the art relying upon the disclosure in this specification and the attached drawings.

What is claimed is:

1. A method for treating injured or diseased bone tissue, the method comprising:
    exposing the injured or diseased bone tissue to a first electric field over a predetermined treatment period, the first electric field ranging from 10 mV/cm to 40 mV/cm and having a first predetermined time period of 2 hours within the predetermined treatment period;
    exposing the injured or diseased bone tissue to a second electric field over the predetermined treatment period, the second electric field ranging from 10 mV/cm to 60 mV/cm and having a second predetermined time period of 12 hours within the predetermined treatment period;
    wherein the first electric field is specific and selective for up-regulating expression of specific bone cell genes in the injured or diseased bone tissue when the injured or diseased bone tissue containing the specific bone cell genes is exposed to the first electric field;
    wherein the second electric field is specific and selective for up-regulating expression of specific bone stem cell genes in the injured or diseased bone tissue when the injured or diseased bone tissue containing the specific bone stem cell genes is exposed to the second electric field;
    wherein the injured or diseased bone tissue is exposed to the first and second electric fields in a sequential manner;
    wherein the injured or diseased bone tissue containing the specific bone stem cell genes is exposed to the second electric field 5 hours after the exposure of the injured or diseased bone tissue containing the specific bone cell genes to the first electric field has ended; and
    wherein the injured or diseased bone tissue containing the specific bone cell genes is exposed to the first electric field 5 hours after the exposure of the injured or diseased bone tissue containing the specific bone stem cell genes to the second electric field has ended.

2. The method according to claim 1, wherein the first electric field is generated from a first capacitively coupled specific and selective signal having a frequency of 30 kHz to 80 kHz and a duty cycle ranging from 12.5% to 100%.

3. The method according to claim 2, wherein the second electric field is generated from a second capacitively coupled specific and selective signal having a frequency of 30 kHz to 80 kHz and a duty cycle ranging from 50% to 100%.

4. The method according to claim 1, wherein the second electric field is generated from a second capacitively coupled specific and selective signal having a frequency of 30 kHz to 80 kHz and a duty cycle ranging from 50% to 100%.

5. The method according to claim 1, wherein the specific bone cell genes and the specific bone stem cell genes whose expression is up-regulated by the first and second electric fields comprise BMP 2 and 4, TGF-beta 1, 2, and 3, FGF-2, BGP and ALP.

6. The method according to claim 5, wherein the up-regulated expression of the specific bone cell and bone stem cell genes increases proteins levels of BMP 2 and 4, TGF-beta 1, 2, and 3, FGF-2, BGP and ALP in the injured or diseased bone tissue.

7. The method according to claim 1, wherein the specific bone cell genes and the specific bone stem cell genes whose expression is up-regulated by the first and second electric fields increases protein levels of BMP 2 and 4, TGF-beta 1, 2, and 3, FGF-2, BGP and ALP in the injured or diseased bone tissue.

8. The method according to claim 1, wherein the first electric field is 20 mV/cm.

9. The method according to claim 1, wherein the frequency of the first capacitively coupled specific and selective signal is 60 kHz.

10. The method according to claim 1, wherein the duty cycle of the first capacitively coupled specific and selective signal is 50%.

11. The method according to claim 1, wherein the second electric field is 20 mV/cm.

12. The method according to claim 1, wherein the frequency of the second capacitively coupled specific and selective signal is 60 kHz.

13. The method according to claim 1, wherein the duty cycle of the second capacitively coupled specific and selective signal is 50%.

14. The method according to claim 1, wherein the predetermined treatment period is 12 to 48 hours.

15. The method according to claim 1, wherein the predetermined treatment period is 48 hours.

* * * * *